US006478965B1

(12) United States Patent
Holtzapple et al.

(10) Patent No.: US 6,478,965 B1
(45) Date of Patent: Nov. 12, 2002

(54) RECOVERY OF FERMENTATION SALTS FROM DILUTE AQUEOUS SOLUTIONS

(75) Inventors: Mark T. Holtzapple, College Station, TX (US); Richard R. Davison, Bryan, TX (US); Torsten Luettich, Essen (DE)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 09/441,211

(22) Filed: Nov. 16, 1999

Related U.S. Application Data

(62) Division of application No. 08/885,841, filed on Jun. 30, 1997, now Pat. No. 5,986,133.

(51) Int. Cl.[7] .............................................. B01D 11/02
(52) U.S. Cl. ............................. lp;1p210/634; 210/802; 210/805; 210/195.1; 210/255; 210/511; 210/521
(58) Field of Search ............................ 210/634, 195.1, 210/255, 511, 522, 521, 802, 805; 366/15, 290, 291

(56) References Cited

U.S. PATENT DOCUMENTS

| | | | | |
|---|---|---|---|---|
| 1,442,306 A | * | 1/1923 | Stonebreaker | 210/255 |
| 2,845,936 A | * | 8/1958 | Boynton et al. | 366/291 |
| 3,079,705 A | | 3/1963 | Ginaven | 34/174 |
| 3,088,909 A | | 5/1963 | Davison et al. | |
| 3,424,675 A | | 1/1969 | Davison et al. | |
| 4,132,651 A | * | 1/1979 | de Jong | 210/522 |
| 4,142,970 A | * | 3/1979 | von Hagel et al. | 210/522 |
| 4,235,602 A | | 11/1980 | Meyer et al. | 23/293 R |
| 4,444,881 A | | 4/1984 | Urbas | 435/139 |
| 4,664,802 A | * | 5/1987 | Lee | 210/522 |
| 4,978,616 A | | 12/1990 | Dean, Jr. et al. | 435/70.3 |
| 5,046,856 A | * | 9/1991 | McIntire | 366/291 |
| 5,050,997 A | | 9/1991 | Sklokin et al. | 366/292 |
| 5,132,456 A | | 7/1992 | King et al. | 562/593 |
| 5,264,623 A | | 11/1993 | Oehr et al. | 562/515 |
| 5,326,474 A | * | 7/1994 | Adams et al. | 210/522 |
| 5,554,301 A | * | 9/1996 | Rippetoe et al. | 210/522 |

FOREIGN PATENT DOCUMENTS

| | | |
|---|---|---|
| CH | 132022 | 3/1929 |
| DE | 3312579 | 10/1984 |
| DE | 19624268 | 4/1997 |
| EP | 112926 | 7/1984 |
| EP | 113378 | 7/1984 |
| EP | 0444338 | 9/1991 |

(List continued on next page.)

OTHER PUBLICATIONS

Chen, et al., "Outline of Raw Sugar Process and Extraction of Juice," *Cane Sugar Handbook*, 12th ed. (1993), pp. 48–102.

(List continued on next page.)

*Primary Examiner*—Robert J. Popovics
(74) *Attorney, Agent, or Firm*—Baker Botts L.L.P.

(57) ABSTRACT

Dilute solutions of fermentation sales may be concentrated by extracting water using low-miscibility, low-molecular-weight secondary and tertiary amines, e.g. triethylamine (TEA), diisopropyl amine (DIA), N,N-diethylmethylamine (DEMA), and mixtures thereof. At 30° C.–55° C., which corresponds to typical fermentation temperatures, these low-molecular-weight amines or their mixtures, can extract large amounts of water from dilute aqueous solutions containing fermentation salts. Thus, dilute fermentation salt solutions can be concentrated by selectively removing water. At these low temperatures, the amine phase contains 20–35% water and a much reduced quantity of fermentation salt. When the temperature is raised, water phases out of the amine, allowing the amine to be recycled and reused to extract additional water. Using this approach, about 82.5% of water can be removed from a 3% dilute solution using conventional multistage, countercurrent extraction, thus providing a 15% concentrated fermentation salt solution.

9 Claims, 10 Drawing Sheets-

FOREIGN PATENT DOCUMENTS

| | | |
|---|---|---|
| EP | 635474 | 1/1995 |
| FR | 642698 | 9/1928 |
| FR | 1064614 | 5/1954 |
| FR | 2227830 | 11/1974 |
| GB | 277975 | 1/1929 |
| GB | 445108 | 4/1936 |
| GB | 1140224 | 1/1969 |
| GB | 2082758 | 3/1982 |
| WO | 9804729 | 2/1998 |

OTHER PUBLICATIONS

Davison, et al., (1960) "Structure and Amine–Water Solubility in Desalination by Solvent Extraction." *J. Chem. Eng.Data*, 5:420–423.

Davison, et al., (1964) "Thermodynamic Cycles For Recovery of Water by Solvent Extraction." *I & EC Process Design and Development*, 3:399–404.

Davison, et al., (1966) "Phase Equilibria of Desalination Solvents: Water–NaCl–Amines." *J. Chem. Eng. Data* 2:304–309.

Davison, et al., (1967) "A Solvent Extraction Desalination Pilot Plant" *Desalination*, 3:17–26.

Ardagh, et al., (1924) "Distillation of Acetate of Lime" *Industrial and Engineering Chemistry*, 16:1133–1139, 1924.

M.J. Playne, "Propionic and Butyric Acids," in Moo–Young, et al., eds., *Comprehensive Biotechnology*, vol. 3, pp. 731–759, No date.

Schultz et al., (1961) "The Pyrolytic Decomposition of Carboxylate Salts to Ketones," *Journal of Chemical Education*. 38:300–301, 1961.

Kirk–Othmer Encyclopedia of Chemical Technology, 3rd Edition, Published by Wiley–Interscience Pub. "Acetone" (1978), vol. 1, p. 180.

Kirk–Othmer Encyclopedia of Chemical Technology, 2nd Edition, Published by Wiley–Interscience Pub. "Calcium Compounds" (1964) 4:6.

Chemical Abstracts "Dipropylketone" Soc. Lefranc et cie. Brit. 216,120, (1923).

Chemical Abstracts "Ketones for motor fuel" E. Depasse, Bull assoc.chim. 60:400–409 (1943).

Chemical Abstracts "General plan for the industrial production of ketones" E. Depasse.Bull.assoc. chim. 62:317–339 (1945).

Conant, et al., (1947) "Aldehydes and Ketones," *The Chemistry of Organic Compounds*, 3rd Edition, pp. 126–127.

Hurd, (1929) "Salts of Organic Acids" *The Pyrolysis of Carbon Compounds*, pp. 480–490.

LeFranc, M.J., "Les Cétones, Carburant A Grand Pouvoir Indétonant, Leur Fabrication Dans Le cadre Des Matieres Premieres Nationales Et 'Imperiales'," Conference faite le Mardi Oct. 28, 1941 au Conservatorie National des Arts et Métiers, pp. 3–27.

Depasse, E., "Les Cétones—Carburants," *Bulletin de l'Association des Chimistes*, vol. 6D, 1943, pp. 400–409.

* cited by examiner

RECOVERY OF FERMENTATION SALTS FROM DILUTE AQUEOUS SOLUTIONS

This application is a divisional application of U.S. application Ser. No. 08/885,841 filed Jun. 30, 1997 and issued as U.S. Pat. No. 5,986,133 on Nov. 16, 1999.

BACKGROUND OF THE INVENTION

1. Field of the Invention

This invention relates to a new and novel technology for isolating fermentation salts from aqueous solution. The method of this invention extracts water from the solution to concentrate fermentation salts, in particular, carboxylate salts such as calcium acetate.

2. Review of Related Art

Numerous manufacturing processes produce aqueous wastes or process streams containing carboxylic acid. These include the manufacture of cellulose acetate, aspirin, camphor, and RDX explosives, as well as semi-chemical wood pulping and other processes that use acetic acid as a raw material or solvent. In addition, there are many manufacturing methods for acetic acid involving recovery of acetic acid from aqueous solution. For example, the principal methods to produce acetic acid are carboxylation of methanol, liquid-phase oxidation of hydrocarbons such as butane and oxidation of acetaldehyde. Earlier processes, such as alcohol fermentation and the destructive distillation of wood, yielded dilute aqueous solutions.

More recently, processes have been proposed to produce acetic acid, or other carboxylic acids, from biomass employing rumen microorganisms that produce dilute aqueous solutions. The concentration of acid in these processes must, of necessity, be dilute, because high acid concentrations inhibit microbial growth.

Several processes have been developed to recover acetic acid from aqueous solutions. These methods include liquid-liquid solvent extraction, azeotropic distillation, and extractive distillation. Simple distillation is not appropriate because (1) the relative volatility between water and acetic acid is close to unity and becomes worse for dilute aqueous acetic acid solutions, and (2) water is the more volatile component, compared to acetic acid; this means all the water has to be vaporized from dilute acetic acid solutions, leading to a large energy cost per unit of acetic acid recovered.

Extractive distillation was used for years in the Suida process to recover acetic acid from pyroligneous acid which contains 6–7% acetic acid. Recycled wood oils were used as the extractant. In acetic acid synthesis plants, azeotropic distillation was used for higher concentration streams. Methyl and ethyl acetates, diisopropyl ether, and benzene are commonly used entrainers for azeotropic distillation, although other esters and ethers, ketones, chlorinated hydrocarbons and alcohols have also been used.

In specific applications of acetic acid manufacturing, other processes might be used. For example, freeze concentration has been used for years as a backyard process for concentrating vinegar. Adsorption with carbon or anion exchangers and chemical derivatization, followed by separation and regeneration of the chemical derivatives, are also available. A conventional derivatization method is the calcium acetate process for recovering acetic acid from pyroligneous acid.

In the calcium acetate derivation process, calcium hydroxide reacts with the acid to form calcium acetate, which is concentrated by evaporation. Then a strong acid, such as sulfuric acid, is added to liberate the free acid. This approach consumes chemicals such as lime and sulfuric acid and produces gypsum as a waste aqueous salt by-product.

Recovery of carboxylic acids from water is one of the oldest applications of solvent extraction. Solvent extraction of carboxylic acid was proposed a century ago. With the development of more sophisticated extraction techniques, such as countercurrent extraction, recovery of residual solvent from the raffinate phase by distillation, and the use of azeotropic distillation to remove coextracted water from the recovered acid, solvent extraction of carboxylic acids from aqueous solutions has replaced the calcium acetate derivation process.

In general, extraction from aqueous solutions has heretofore been the most favored approach to recover acetic acid, except for feeds (aqueous solutions) above about 80% (w/w) acetic acid content, where azeotropic distillation is preferred. Based on the development of new extractants, extractive processes, and the change in the economic structure, extraction is now favored for feeds containing acetic acid below 30% (w/w); extractive distillation is preferred for feeds in the 30–80% (w/w) range; and azeotropic distillation and simple fractionation (distillation) are appropriate for more concentrated feeds.

In the literature, solvent extraction has been the main theme for recovering carboxylic acid from dilute aqueous solutions. Because the solvents tend to be partially water soluble, a unit operation is required to remove or recover residual solvent from the raffinate. Typical extraction processes recover carboxylic acid from water using three unit operations: the extractor, a solvent regenerator, and a process to recover free carboxylic acid. In a conventional extraction process, one first extracts acid into the organic phase, followed by back-extracting acid into an aqueous phase, thus regenerating the organic phase. In the regeneration process, the aqueous phase used to back extract acid from the extract is usually an aqueous solution containing a low-boiling alkaline solvent (e.g. trimethylamine) which can be easily evaporated. Using this process, carboxylic acid can be separated and recovered.

Among the extractants used to recover carboxylic acid are reactive, basic extractants (e.g. tertiary amines or phosphine oxides) that can be used to gain greater solvent capacity and selectivity with respect to water and carboxylic acid. Although solvent extraction is a potentially attractive process for carboxylic acid recovery, it is usually deterred by the high affinity of these acids for water. Previous workers have characterized some extractants that provide a relatively high equilibrium distribution coefficient for extracting carboxylic acid from aqueous solution. A high equilibrium distribution coefficient allows the use of lower solvent-to-feed flow rates.

Primary amines are too soluble in water to be used with aqueous solutions. Secondary amines are subject to amide formation upon regeneration by distillation. Consequently, long-chain tertiary amines have become the most favored extractant for recovering carboxylic acid from dilute aqueous solutions. With the use of appropriate diluents and swings of temperature or pH, tertiary amine extractant systems have become more powerful agents for carboxylic acid recovery.

Desalination

Solvent extraction has also been proposed as a method to recover potable water from sea water or brackish water. Extracting sea water with an amine solvent produced a concentrated brine (raffinate) and an extract containing a mixture of water and amine. Clear water was recovered by heating the water-laden extract to a higher temperature at which the solubility of solvent in water was greatly reduced. Previous discussions concerning the solvent extraction of water have been published by Davison et al. (see Davison, et al., "Structure and Amine-Water Solubility in Desalination by Solvent Extraction," *J. Chem. Eng. Data* 1960, 5, 420–423; Davison, et al., "Thermodynamic Cycles For Recovery of Water by Solvent Extraction," *I&EC Process Design and Development,* 1964, 3, 399–404; Davison, et al., "Phase Equilibria of Desalination Solvents: Water-NaCl-Amines," *J. Chem. Eng. Data.* 1966, 2, 304–309; Davison, et al., "A Solvent Extraction Desalination Pilot Plant," Desalination, 1967, 3, 17–26; Davison and Hood, U.S. Pat. No. 3,088,909; and Davison and Hood, U.S. Pat. No. 3,424,675.) ps Carboxylic Acids from Biomass There has been increasing interest in using anaerobic bacteria to produce organic acids from biomass. A dilute aqueous stream of carboxylic acid can be produced by fermenting lignocellulosic biomass. The concentration in the fermentation broths is limited by the autotoxicity of the acid to acetogenic fermentation bacteria. It may be as high as 6% (w/w), but concentrations of 2–4% are more typical. Product inhibition can be reduced by continuously removing the acid.

Extractive fermentation has been proposed to remove the inhibiting acid in situ and thus increase the bioreactor productivity. However, at the pH where the microbes grow (about 6.8), only 1% is undissociated acid; the rest is salts that will not be extracted, especially by tertiary amines. Most extractants work efficiently only at acidic pH, yet acidogenic anaerobes generally have poor growth rates below pH 6. Thus, extractive fermentation is not viable to remove acid product in situ.

Moreover, after solvent-extracting carboxylic acid from the aqueous fermentation broth using high-molecular-weight tertiary amines, the acid-amine complexes must be broken to recover the free acid and recycle the amine extractant, either by azeotropic distillation or back-titration. For recovering carboxylic acid from dilute aqueous solutions, the extraction-regeneration process requires both acid addition to adjust the pH and an extra solvent-extraction process to regenerate the primary extractant. Furthermore, the tertiary amines extractant (or phosphine oxide extractant) must necessarily have a high molecular weight to make it immiscible in water. However, it is impossible to make these extractant amines perfectly immiscible in water, so some extractant is always present in the aqueous phase. Because of their high molecular weight, these extractants are non-volatile and cannot be recovered by stripping in a distillation column. Therefore, additional extractants must be added to replace that which is lost, thus incurring additional expense.

Necessarily, when produced by fermentation, the acid product is primarily present as a carboxylate salt. The pH of an aqueous solution of carboxylic acids is ordinarily low because the acids dissociate releasing hydronium ions in aqueous solution. To sustain active fermentation, it is necessary to add a neutralizing agent (i.e., lime or limestone) that reacts with the hydronium ion and maintains a pH near to neutrality where microbial activity is greatest. Near neutrality, only about 1% of the product is carboxylic acid; the remainder is present as the carboxylate salt. Therefore the traditional technologies for recovering carboxylic acids are not easily applied, and a need exists for developing of alternative technologies.

SUMMARY OF THE INVENTION

Recovery of carboxylic acid from fermentation broths with conventional solvent extraction is not economical, especially when ideal extractants (i.e. those that can extract carboxylate salt into the organic phase) are not available currently. Therefore, the inventors have developed a new process to concentrate fermentation broths by removing water from dilute aqueous solutions of the carboxylate salt (typically the calcium salt) rather than the conventional approach of removing acid from water. This novel extraction removes water from the aqueous phase, but selectively retains salts in the aqueous phase. As water is extracted into the organic phase, salts concentrate in the aqueous phase. The water can be recovered from the organic phase by raising the temperature which causes the water to phase out of the organic phase. This recovered water can be returned to the fermentor after stripping residual organic material. In the process of the invention, residual organics are also stripped out of the concentrated product.

This invention relates to a new and novel technology for isolating carboxylate salts and/or acids from an aqueous solution. Because it is difficult to extract acid from near-neutral pH fermentation broth, this invention provides method of extracting the water instead, thereby concentrating the organic acid and salt solutions.

This invention further relates to the manufacture of carboxylic acid in which the improvement is to concentrate dilute aqueous carboxylate salt solutions (2–5%) produced via fermentation. In particular, this invention pertains to the manufacture of carboxylic acid wherein the salt of carboxylic acid, manufactured by fermentation (i.e., by rumen microorganisms, by mixed-acid fermentation, or by pure-culture fermentation) is recovered from the aqueous solution and the extractant is conveniently and economically recycled to the extraction process. The carboxylate salts need not be monocarboxylates and may contain other functional groups, as for example, hydroxyl groups. The carboxylate salts need not be derivatives of saturated hydrocarbons, but may contain unsaturation. Typical carboxylate salts that can be manufactured by fermentation and recovered by the method of this invention include acetates, propionates, lactates, succinates, and the like.

DETAILED DESCRIPTION OF THE INVENTION

Figure 1:
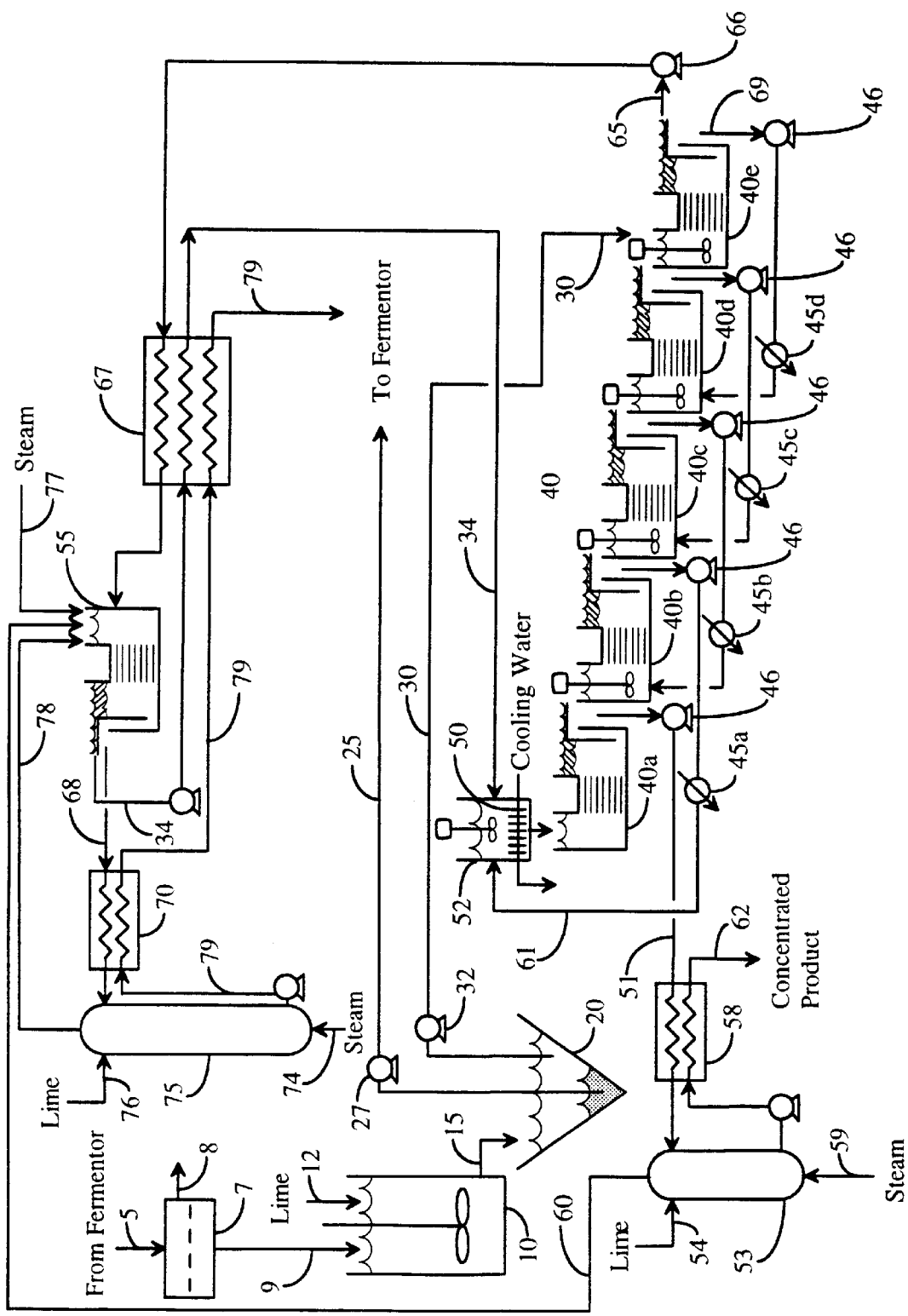
FIG. 1 shows a schematic representation of a process (Process A) for concentrating fermentation salts.

This invention, in a preferred embodiment, is a process in which fermentation broth, which contains dilute carboxylate salt, is contacted with a low-molecular-weight secondary or tertiary amine which has a high affinity for water and a low affinity for carboxylate salt. From previous work on desalination (Davison et al., Phase Equilibria of Desalination Solvents: Water-NaCl-Amines. *J. Chem. Eng. Data.* 1966, 2, 304–309), two low-molecular-weight tertiary amines, i.e. triethylamine (TEA) and N,N-diethylmethylamine (DEMA), were chosen because of their superior capacity to selectively extract water from aqueous salt solutions in the proper temperature ranges. The temperature of the water-laden amine is increased by about 20–30° C. which causes the water to separate from the amine and form another phase. The carboxylate salt remains in the fermentation broth and becomes concentrated. Residual amines in aqueous phases are recovered by adding alkali (e.g., lime) to raise the pH, thus making the amines volatile. The residual amines are then recovered by stripping them out in a distillation column.

In the past, extraction of water from a salt solution has been applied to the recovery of drinking water from salt water, i.e., sea water, brackish water, or the like. The present invention may be distinguished from this previous application as follows:

1. In the fermentation, one can select the cation which accompanies the carboxylate. Divalent ions (i.e., calcium) are excluded from the amine extractant more fully than monovalent ions (i.e., sodium, ammonium). Thus, by choosing a divalent cation, the water can be more selectively removed from the salt solution. In contrast, the cations in sea water or brackish water are dictated by nature and typically are monovalent cations. As a result, the water and salt are not separated efficiently.

2. In the present invention, the salt is the desired product, whereas in the previous process, the water was the desired product. The carboxylate salt is much more desirable and valuable than the water, giving the present process favorable economics. In contrast, amine extraction of water is not economically attractive.

3. In the drinking water process, the water product must be virtually free of salt to be acceptable for human consumption. This requires the use of a large rectification section in addition to the stripping section. These added rectification stages incur additional expense. In contrast, the present invention can tolerate higher concentrations of salt in the water stream because the water is simply recycled to the fermentor. Therefore the rectification section can have many fewer stages or be eliminated altogether.

4. Complete amine recovery from all aqueous streams is critical for good economics; otherwise, the expense of replacing the lost amine is too great. The amine is recovered by stripping it from the aqueous stream in a distillation column. To ensure that the amine is present as volatile free amine as opposed to non-volatile amine salts, it is necessary to raise the pH by adding alkali. In our invention, this is easily accomplished by adding lime to the aqueous streams. There is little expense associated with this because a neutralizing agent must be added to the fermentor anyway. Thus, there are synergies and efficiencies associated with coupling the amine with the fermentor. In contrast, addition of alkali to the drinking water process incurs significant expense not only for the alkali, but also for its recovery; it is not acceptable for the alkali to remain in the drinking water product. Complete amine removal from drinking water is essential due to its potential health effects.

Carboxylate salts which can be manufactured by fermentation and concentrated by the method of this invention include salts of acetic acid, propionic acid, lactic acid, succinic acid, and the like. This method is also applicable to dilute aqueous solutions of carboxylate salts produced by methods other than fermentation.

According to the present invention, the organic phase comprises an organic secondary or tertiary amine. Preferred amines include low-molecular-weight alkyl secondary or tertiary amines or mixtures thereof. Preferred amines are amines of the formula $R_3N$, wherein R is methyl, ethyl, n-propyl, or isopropyl. Most preferred amines are triethyl amine, N, N-diethylmethyl amine, and mixtures of these two amines. The use of various ratios of the two amines provides an extraction system that possesses different lower critical temperatures. By selecting the appropriate amine compositions, it is possible to operate the extraction process at any proposed temperature from 10° C. to 70° C. Within this temperature range are both mesophilic and thermophilic acid-forming bacteria which gives flexibility in developing an appropriate fermentation system.

The most favored carboxylic-acid-producing microorganisms that use lignocellulosic biomass are: (i) mesophilic (40° C.) mixed cultures obtained from either cattle rumen or anaerobic sewage digesters, and (ii) thermophilic (55° C.) mixed cultures from anaerobic sewage digesters. Another promising thermophile is the cellulytic organism Clostridium thermocellum which produces both acetic acid and ethanol generally in roughly equal amounts. Suitable fermentation processes are described in greater detail in application Ser. No. 08/885,896, entitled "Method for Conversion of Biomass to Chemicals and Fuels,"filed concurrently herewith and incorporated herein by reference.

To avoid unnecessary heating or cooling of fermentation broths, the extraction is operated at or near the fermentation temperature, as for example at or near 40° C. or 55° C. depending on the microorganisms.

When the aqueous phase contacts the low-molecular-weight amine, the pH rises forming calcium hydroxide. Because calcium hydroxide is fairly insoluble, some precipitates thus removing calcium ions from solution. These ions are replaced with amine ions to form amine-carboxylate complexes in the aqueous phase. The formation of water-soluble amine carboxylate is handled by adding calcium hydroxide to the strippers so calcium can replace the amine as the amine volatilizes.

Typically, lignocellulosic biomass is fermented to yield a dilute solution of carboxylate salts from which water may be extracted using low miscibility, organic extractants. Preferably these organic extractants are low-molecular-weight secondary or tertiary amines, e.g. triethylamine (TEA), di-isopropyl amine (DIA), and N,N-diethylmethylamine (DEMA). At 40° C.–55° C., which corresponds to typical fermentation temperatures, these low-molecular-weight tertiary amines or mixtures thereof can extract large amounts of water from dilute aqueous solutions containing carboxylate salts. Thus, dilute carboxylate solutions can be concentrated by selectively removing water. At lower temperatures, the amine phase contains 20–35% water and negligible carboxylate salt. When the temperature is raised, water phases out of the amine, allowing the amine to be recycled and reused to extract additional water. In a typical example, using this approach, about 82.5% of water can be removed from a 3% dilute solution using conventional multi-stage, countercurrent extraction, thus providing a 15% concentrated carboxylate salt solution.

A typical embodiment of this invention may be described by reference to FIG. 1. Fermentation broth 5 is filtered in solids separator 7 (e.g. filter, hydroclone, centrifuge, settler) to remove insoluble residues 8 (e.g. cells, unreacted biomass). The solid-free solution 9 is sent to mixer 10 where lime 12 is added to increase the pH to approximately 11.5. The high pH precipitates minerals and organics (e.g. proteins, carbohydrate polymers, etc.). The slurry 15 is sent to solids separator 20 (e.g. filter, hydroclone, centrifuge, settler) where the precipitate 25 is removed by pump 27. FIG. 1 shows the precipitate being returned to the fermentor. Alternatively, it could be processed further to separate the minerals, protein, and carbohydrate polymers depending upon the value of these components.

Using pump 32, precipitate-free liquid 30 is sent to a series of mixer/decanters 40 where it will be contacted countercurrently with water-lean amine 34. (Although FIG. 1 shows a series of mixer/decanters are used to countercurrently contact the amine and water phases, other contacting devices may be used, such as packed columns, rotating-disc columns, oscillating-plate columns, etc. The choice of the appropriate contactor depends upon scale; mixer/decanters are preferred for large flow rates. Although FIG. 1 shows five mixer/decanters, fewer or more may be used.) Precipitate-free liquid 30 is sent to mixer/decanter 40e where it is mixed with amine from mixer/decanter 40d. The amine absorbs some water from the water phase thus increasing its salt concentration.

Figure 2:
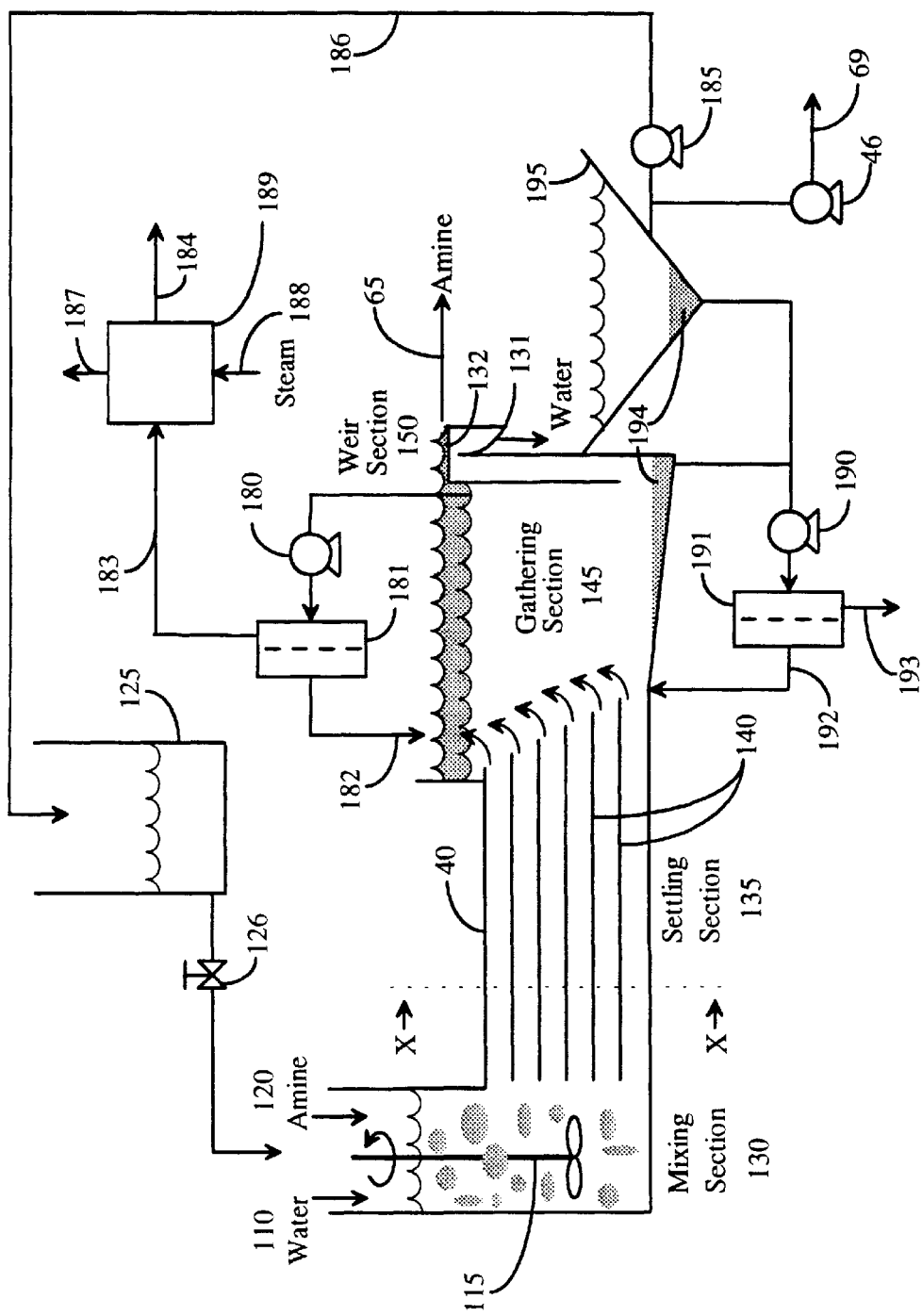
FIG. 2 shows a schematic representation of a mixer/decanter that employs periodic cleaning.

As shown in FIG. 2, the amine/water mixture flows through a series of parallel plates 140 in the mixer/decanter and enters a gathering section 145 where the amine phase and water phase separate. The amine phase, having a lower density, is recovered from the top, and the water phase is recovered from the bottom. Weirs 150 are set to regulate the height of the amine/water interface. Amine flows over the top and water is recovered from the underflow.

In the embodiment shown in FIG. 1, water-rich amine phase 65 is sent to separator 55 to recover the absorbed water. Water phase 69 is sent to mixer/decanter 40d where it is mixed with amine phase from mixer/decanter 40c which absorbs additional water further concentrating the water phase. This process is repeated in the other mixer/decanters. As the water phase moves from right to left, its salt concentration increases. As the amine phase moves from left to right, its water content increases.

In each of the mixer/decanters, water and amine are mixed. Because there is a particularly large heat of mixing released when water-lean amine 34 is mixed with water 61, mixing for mixer/decanter 40a is performed in a separate vessel 52 which is provided with cooler 50. Other mixer/decanters (40b through 40e) also have a heat of mixing, but it is much less and is removed by heat exchangers 45 which regulate the temperature. Water pumps 46 cause the water to flow through the heat exchangers and on to the adjacent mixer/decanter 40. Pumps are required only for the water flow; by arranging the mixer/decanters 40 at successively declining elevations, the amine will flow by gravity eliminating the need for amine pumps.

Water stream 51, which has the highest salt content, has dissolved amine which must be removed. It is preheated in countercurrent heat exchanger 58 and is sent to stripper 53 where steam 59 vaporizes the amine. To ensure that amine is present as the volatile unionized species, rather than a nonvolatile ionized species, lime 54 is added to raise the pH. The volatile amine exits in stream 60 which also contains steam. Stream 60 is directed to separator 55 where it provides some of the latent heat needed to separate water and amine. Amine-free concentrated product 62 is ready for further downstream processing.

Pump 66 transports water-rich amine 65 to countercurrent heat exchanger 67 where the temperature is raised. In heat exchanger 67, as the temperature is raised, the water begins to phase out of the amine. This process is completed in separator 55 where additional heat, in the form of steam 77, is supplied to raise the temperature and supply the latent heat necessary to separate the water from the amine. Separator 55 has a design similar to the mixer/decanters 40, except that a mechanical mixer is not required.

Water phase 68 issuing from separator 55 contains dissolved amine. It is preheated in countercurrent heat exchanger 70 and sent to stripper 75 where steam 74 vaporizes the amine. To ensure that amine is present as the volatile unionized species, rather than a nonvolatile ionized species, lime 76 is added to raise the pH. The volatile amine exits in stream 78 which also contains steam. Stream 78 is directed to separator 55 where it provides some of the latent heat needed to separate water and amine. Amine-free water 79, which has a very low salt content, is cooled in countercurrent heat exchanger 70 and countercurrent heat exchanger 67 and is returned to the fermentor. If excess water must be purged from the system, a side stream of water can be removed from stream 79 and sent to the waste water treatment plant for ultimate discharge. Water-lean amine 34 issuing from separator 55 is pumped through countercurrent heat exchanger 67 and mixes with water in mixer 52.

Mixing and decanting are normally performed in separate pieces of equipment. Mixing is typically performed in a stirred tank, pump, or an in-line static mixer. Decanting can be performed in a quiet tank or in a parallel plate separator. Parallel plate separators were first described by Hazen in 1904.

In a preferred embodiment, this invention provides a device that mixes raffinate and extract phases together and then decants them to achieve separation. It has been discovered that decanting occurs quickly in a horizontal tube. In order to capitalize on this observation, this invention provides the device shown in FIG. 2. Among the unique features of this embodiment are that it combines both a mixer and decanter into a single device. FIG. 2 shows a detailed sideview of the mixer decanter 40. It is divided into four major sections: mixing section 130, settling section 135, gathering section 145, and weir section 150.

Figure 3:
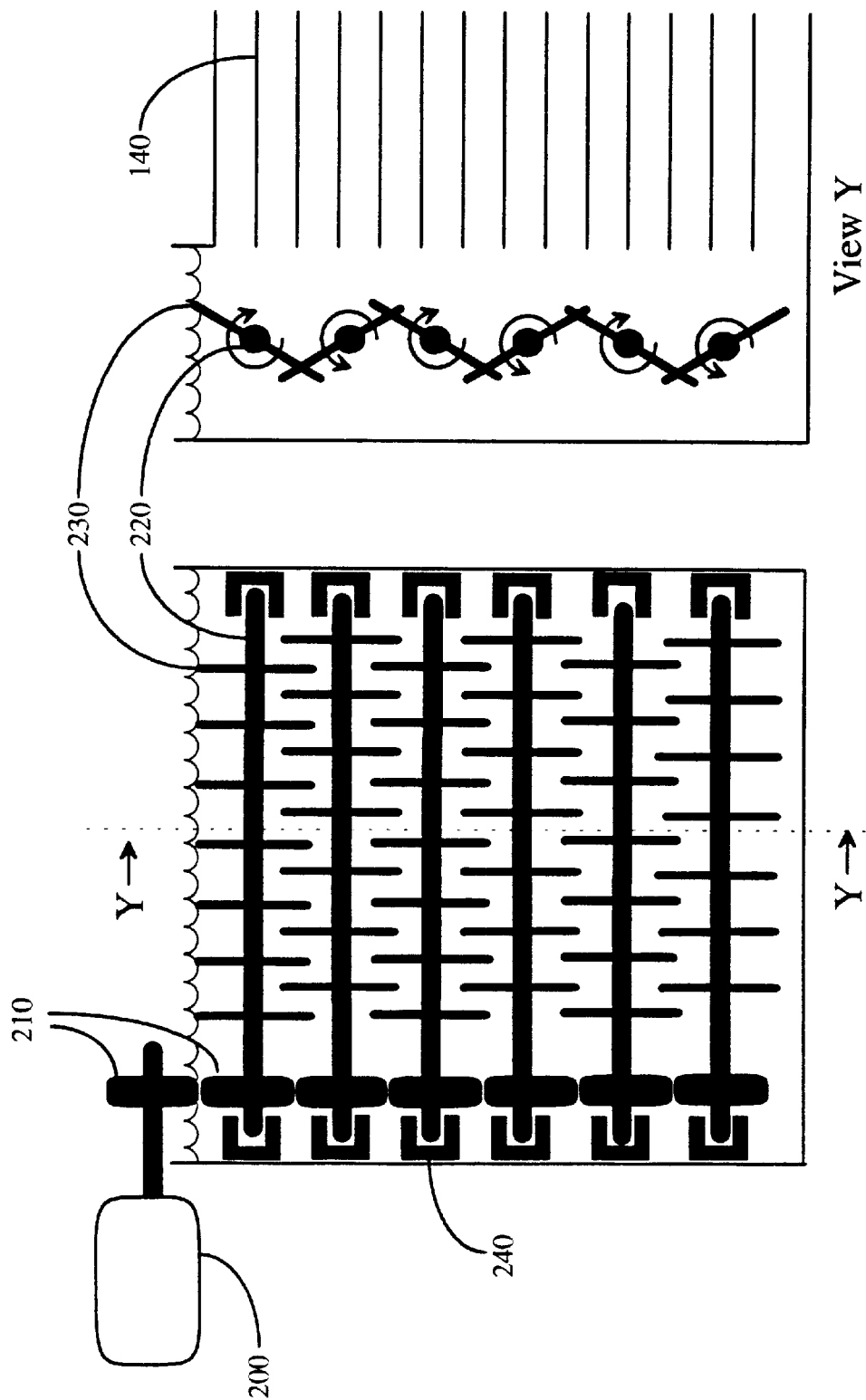
FIG. 3 shows a schematic representation of a method for achieving uniform gentle mixing of amine and water.

In the mixing section 130, water 110 and amine 120 are evenly mixed together using impellor 115. Because equilibrium is quickly and easily reached, mixing can be very gentle; therefore, emulsions are not formed and the amine phase quickly decants from the water phase. Even though the amine flowrate is about five or six times greater than the water flowrate, water is the continuous phase and amine is the discontinuous phase. This type of operation allows the amine residence time to be very short which reduces the amine inventory and lowers costs. FIG. 2 shows an impellor providing the mixing. FIG. 3 shows an alternative embodiment using a series of "fingers" 230 mounted on a shaft 220 which is held in place using bearings 240. The shafts are driven by motor 200 which rotates gears 210. Adjacent shafts rotate in opposite directions. The fingers on adjacent shafts are interspersed allowing uniform mixing to occur in mixing section 130. The degree of mixing is determined by the rotational speed and the number of fingers per shaft. To promote even mixing, water and amine may be introduced at multiple points in the mixing section 130.

Figure 4:
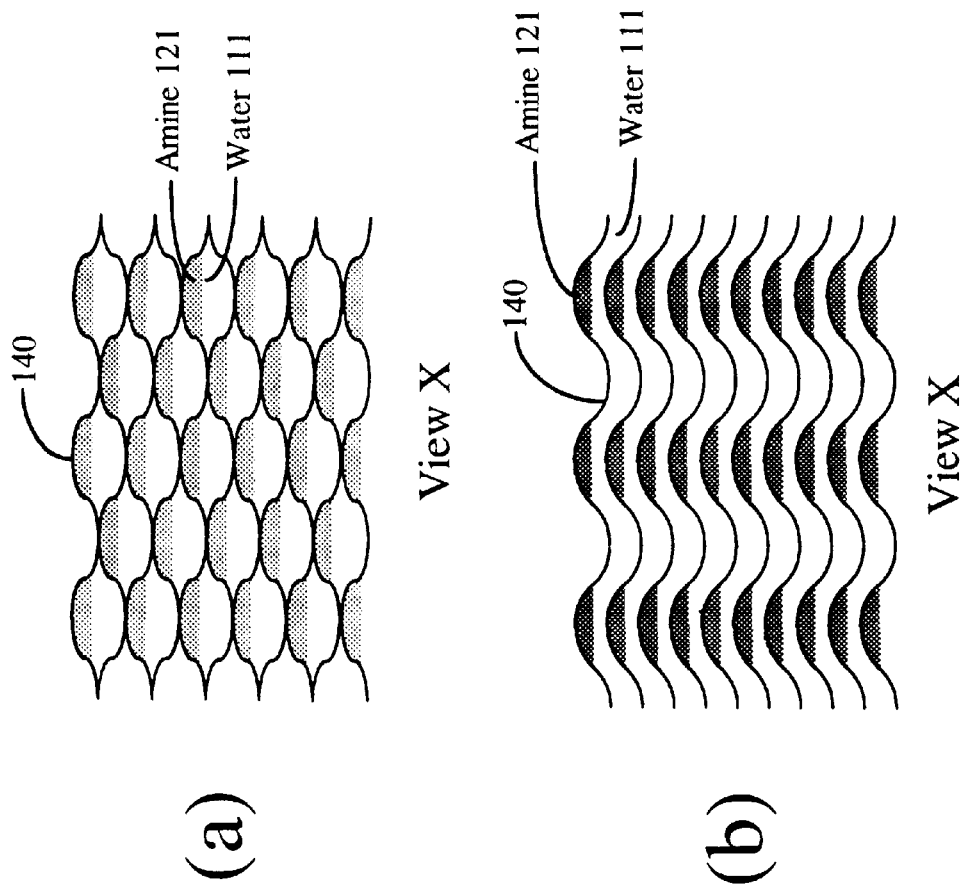
FIG. 4 shows two possible configurations for parallel plates used to settle amine and water.

As shown in FIG. 2, the settling section 135 consists of a series of parallel plates 140. The parallel plates have a short settling distance allowing the dispersed phases from the mixing section 130 to quickly coalesce. The short amine residence time in settling section 135 reduces the amine inventory which saves capital costs. FIG. 4 shows two possible embodiments of parallel plates. Both FIGS. 4a and 4b use rippled plates, much like those used as siding on buildings. The two versions differ only in the orientation of the parallel plates 140. In FIG. 4a, every other plate is in the same orientation and in FIG. 4b, every plate is in the same orientation. The plate orientation shown in FIG. 4b is preferred because it allows for very close plate spacing even if there are deep ripples. Close plate spacing ensures the flow is laminar, rather than turbulent, which promotes coalescence. As the amine/water phases flow between the parallel plates, each phase coalesces; the amine phase (being less dense) floats to the highest point and the water phase (being more dense) sinks to the lowest point.

FIG. 2 shows that gathering section 145 is simply a quiescent tank. The gathering section 145 is operated with water as the continuous phase and amine as the dispersed phase. As coalesced amine exits from settling section 135, it quickly floats to the top. To reduce interference with adjacent amine as it flows to the top, parallel plates 140 are successively longer lower in the settling section 135. Solids, such as precipitated calcium hydroxide, settle in the gathering section and are removed by pump 190 and sent to solids separator 191 (e.g. filter, hydroclone, centrifuge). The solids are returned to strippers 75 or 53 to provide the lime necessary to volatilize amine.

FIG. 2 shows that weir section 150 consists of overflow weir 132 and underflow weir 131. Overflow weir 132 sets the height of the upper surface of the amine and underflow weir 131 sets the height of the amine/water interface. Amine phase flows over overflow weir 132 and water phase flows over underflow weir 131. To reduce the amine residence time (and hence reduce the amine inventory), the underflow weir 131 is adjusted to minimize the thickness of the top amine layer.

A "rag layer" may collect at the amine/water interface, so pump 180 is included to draw fluid from the amine/water interface and direct it to solids separator 181 (e.g. filter, hydroclone, centrifuge). Amine 182 is returned to gathering section 145. Using steam 188, separated solids 183 would be stripped of amine in chamber 189. Exiting vapors 187 are sent to separator 55 to provide energy needed to phase separate water from amine. Depending upon the nature of separated steam-stripped solids 184, they may be returned to the fermentor, or they may be disposed of in an appropriate manner.

Because the flow through parallel plates 140 is low, solids (such as precipitated calcium hydroxide) eventually may plug settling section 135. To clean parallel plates 140, amine flow 120 would be discontinued. Valve 126 would be opened allowing water from elevated holding tank 125 to quickly flow by gravity through parallel plates 140 causing turbulent flow that entrains any solids that settled in the parallel plates. Entrained solids 194 are collected in gathering section 145 or surge tank 195. After the cleaning operation is performed, amine flow 120 resumes and mixer/decanter 40 continues as before. During normal operation of mixer/decanter 40, pump 185 slowly returns water to elevated tank 125 in preparation for the next cleaning cycle.

Figure 5:
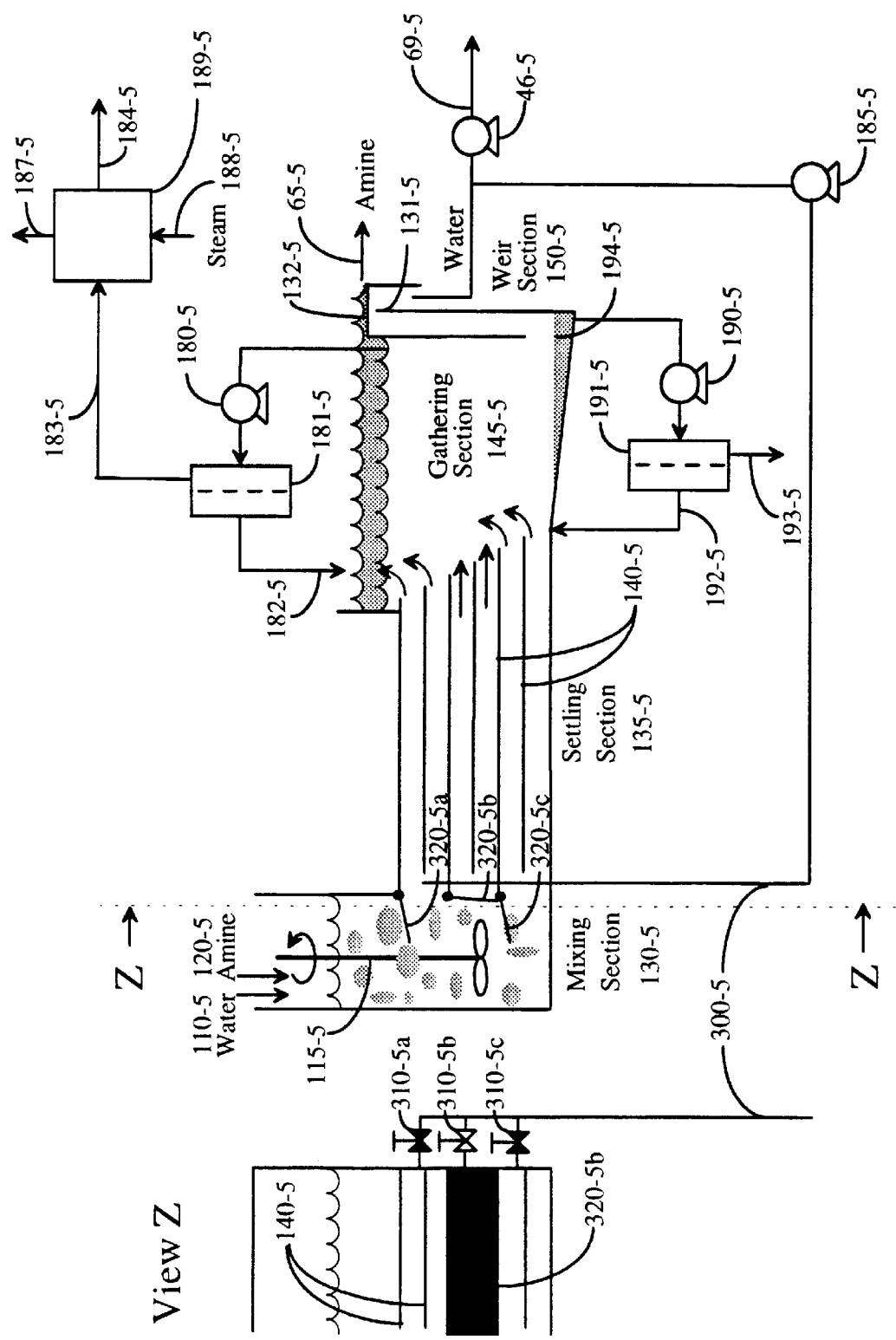
FIG. 5 shows a schematic representation of a mixer/decanter that employs continuous cleaning.

In FIG. 2, tanks 125 and 195, used to clean the parallel plates 140, must be large in order to develop the tubulent flow required to entrain solids. FIG. 5 shows an alternate embodiment in which parallel plates 140-5 are continuously cleaned where, advantageously, the cleaning equipment is considerably smaller. Louvers 320-5 may be opened or closed. When closed, a section of parallel plates 140-5 is isolated allowing it to be cleaned while the remainder of the parallel plates may perform their usual function. As shown in FIG. 5, louvers 320-5a and 320-5c are open allowing the upper and lower sections of parallel plates 140-5 to perform their usual function; however, louver 320-5b is closed, allowing the middle section of parallel plates 140-5 to be cleaned. As shown from View Z, valve 310-5b is opened whereas other valves 310-5a and 310-5c are closed. This valve arrangement allows high velocity water, obtained from pump 185-5, to entrain solids in the middle section of parallel plates 140-5 and discharge the solids to gathering section 145-5 where they settle and are collected by pump 190-5.

Compared to other technologies, the mixer/decanter described in FIGS. 2 to 5 provides numerous advantages. Compared to separate mixers and decanters, less piping is required. The degree of mixing is regulated by the agitation rate, and unlike the use of a pump as a mixer, very gentle mixing can be achieved. Furthermore, the degree of mixing is independent of the addition rate of amine and water giving greater control than an in-line static mixer. By incorporating flow between parallel plates 140, the phases separate much more quickly than in a quiet tank. To facilitate complete separation of water/amine, the water residence time can be lengthened by increasing the volume of gathering section 145. In contrast, the amine residence time can be short by adjusting the height of weir 131 so that the amine layer is very thin.

Heat transfer is an important factor in optimizing this process. One preferred method for heating and cooling the amine-containing streams employs countercurrent heat exchangers 67. Plate-and-frame heat exchangers are generally preferred for low capital cost relative to heat transfer (heat transfer coefficients of 625 Btu/(ft$^2$·h·° F.) can be achieved). Additional energy savings may be achieved by using very close approach temperatures in the hot and cold streams. For example, adding surface area to go from log-mean deltaT (LMDT) of 6.5° C. to 4.1° C. generates energy savings which more than pay for the increase in capital expense.

Using countercurrent heat exchanger 67 in the amine-dewatering process, only sensible heat is required on the water-lean side, but the water-rich side has both sensible and latent heat requirements. As the water-rich side warms, the water phases out of the amine, and the latent heat requirement effectively raises the heat capacity. As a consequence, the temperature difference could be, e.g., only 1° C. on one end of the heat exchanger, but 10.9° C. at the other end.

The process described in FIG. 1 may be considered a "base case" which has the lowest capital cost, but also the lowest energy efficiency. Other process alternatives that have a higher energy efficiency are described in Table 1.

TABLE 1

Energy Costs

| Process | Description | *Steam Cost ($/lb HAc) |
|---------|-------------|------------------------|
| A | Base Case | 0.010 |
| B | Single-stage vapor-compression heat pump | 0.0047 |
| C | Multiple-stage steam ejector heat pump | 0.0037 |

*steam cost = $3/million Btu
acetic acid concentration = 22 g HAc/L
total acid concentration = 30 to 35 g/L Process A is a "base-case" that has minimal capital cost, but is not energy efficient (see FIG. 1). Process B is more efficient because it employs a vapor-compression heat pump to transfer the heat of mixing (released at the absorption temperature, e.g. 40° C.) to the separator (which operates at a higher temperature, e.g. 60° C.). Unfortunately, because the density of the vapor is so low, very large compressors are required, incurring capital expense which may be prohibitive. Process C reduces the capital cost of heat pumps by employing low-cost steam ejectors rather than mechanical compressors. The steam is supplied from the strippers. Because steam ejectors are inefficient at high compression ratios, multiple-stage ejectors are employed allowing many of the stages to have a very low compression ratio. The multiple stages employed in Process C allow it to have the lowest energy cost. Because ejectors are very inexpensive, the capital cost of Process C is only slightly above Process A.

Figure 6:
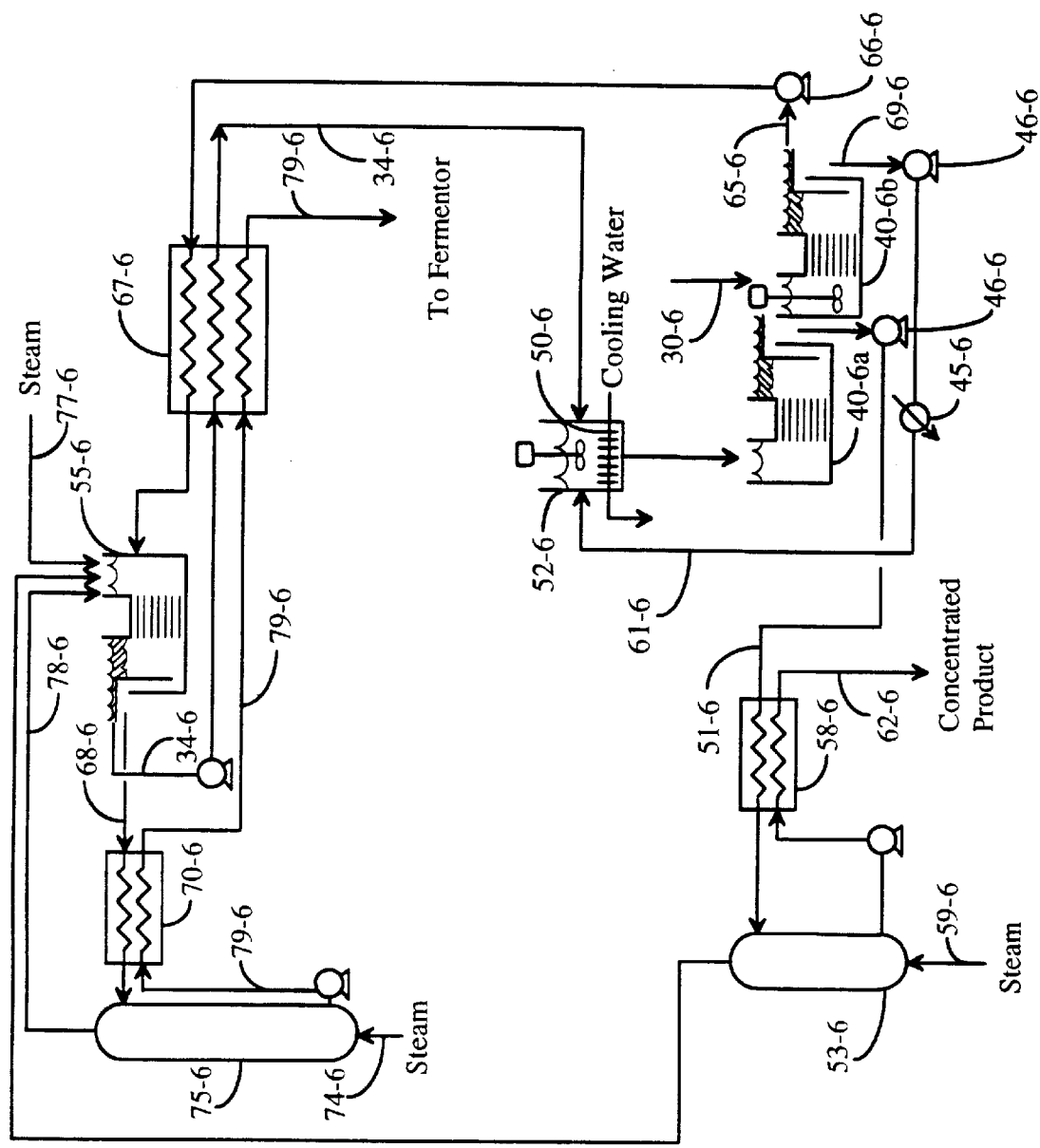
FIG. 6 shows a simplified schematic of Process A which indicates the equipment that affects process energetics.

FIG. 6 is a simplified version of Process A which shows the equipment that affects the process energetics. For simplicity, only two extraction stages are shown. Separator 55-6 is the major consumer of energy. It requires two forms of energy: (1) latent heat needed to phase water out of the amine, and (2) sensible heat needed to raise the temperature of the water-rich amine from the extraction temperature (e.g. 40° C.) to the separation temperature (e.g. 60° C.). By making countercurrent heat exchanger 67-6 sufficiently large, the sensible heat demands by separator 55-6 are minimized. The latent heat demands are mostly met by the overhead vapors from strippers 53-6 and 75-6. Some additional energy can be provided by steam 77-6 which may result from other unit operations in the plant, such as multiple-effect evaporators or distillation column condensers. Provided countercurrent heat is exchanger 67-6 is sufficiently large, water-lean amine 34-6 will be cooled to approximately the extraction temperature (e.g. 40° C.). Cooler 50-6 is required to remove the heat of mixing resulting from mixing water-lean amine 34-6 and water 61-6. Ideally, given an infinitely large countercurrent heat exchanger 67-6, the heat added to separator 55-6 is removed using cooler 50-6. In actuality, given a countercurrent heat exchanger 67-6 of finite size, some additional heat must be added to separator 50-6 to provide sensible heat. Similarly, some additional cooling must be provided by cooler 50-6 to remove sensible heat.

FIG. 7 shows Process B, again emphasizing only that equipment which affects process energetics. In this case, rather than rejecting the heat of mixing to cooler 50-6, a vacuum is pulled on mixer 52-7 by compressor 300-7 which causes some amine and water to evaporate cooling the liquid to the extraction temperature (e.g. 40° C.). The compressed vapors 315-7 are sent to separator 55-7 which operates at its vapor pressure. Compressed vapors 315-7 condense in separator 55-7 and provide the heat required to phase the water out of the amine. Compressor 300-7 is driven by steam turbine 310-7 which is fed with high-pressure steam 320-7 and rejects low-pressure steam 325-7. The low-pressure steam is sent to amine strippers 75-7.

Figure 7:
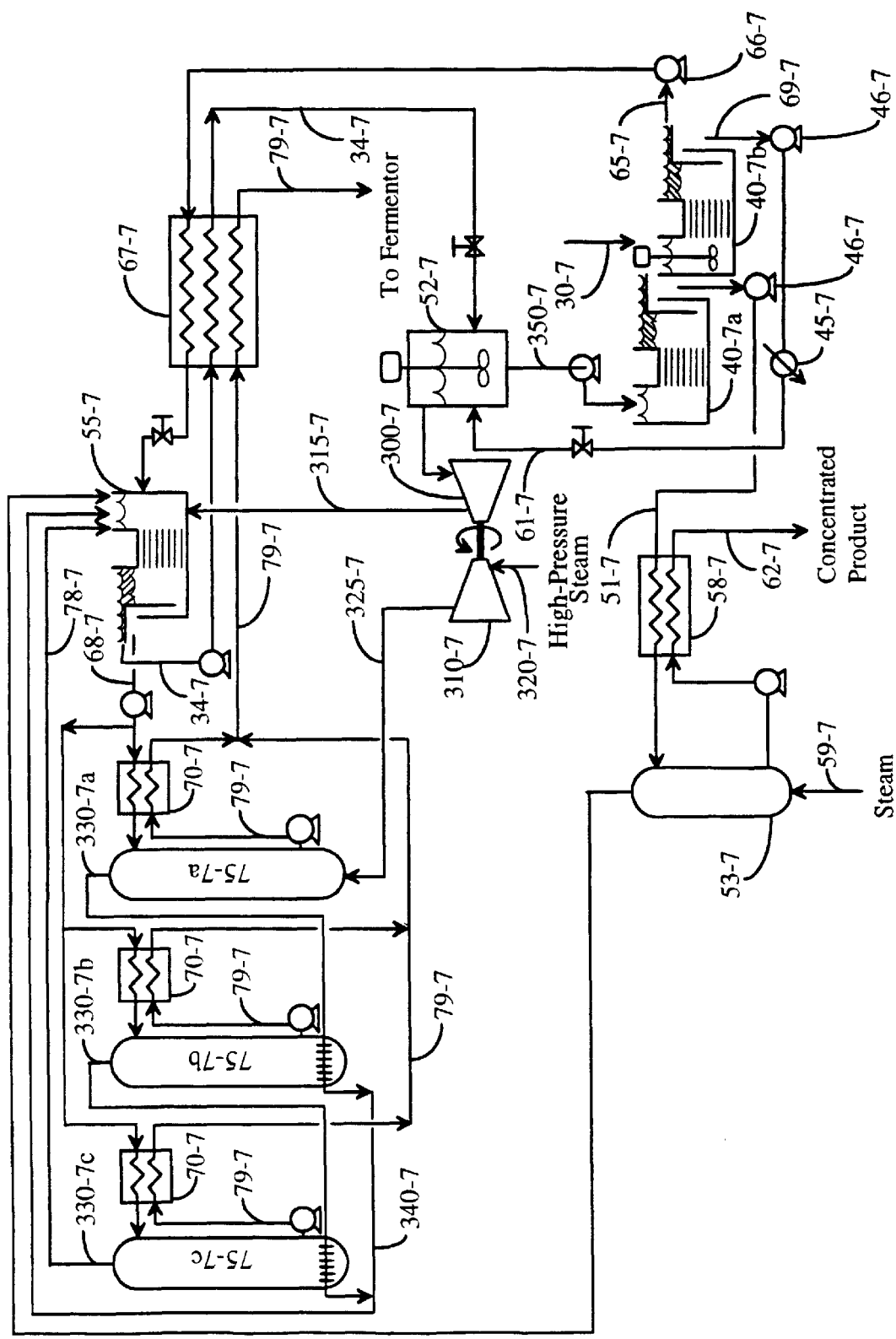
FIG. 7 shows a simplified schematic of Process B which indicates the equipment that affects process energetics.

Because Process B is more energy efficient than Process A, a single stripper would generate more vapors than are need by separator 55-7. Therefore, the stripping operation is performed in multiple effects. Stripper 75-7a is operated at a higher temperature and pressure than stripper 75-7b which, in turn, is operated at a higher temperature and pressure than stripper 75-7c. FIG. 7 shows three strippers, but fewer or more could be used depending upon the cost of capital and the cost of energy. Also, stripper 53-7 could be operated in multiple effects, but it is much smaller and has less impact on process energetics. Low-pressure steam 325-7 from turbine 310-7 is sent to stripper 75-7a which operates at the highest temperature and pressure. Overhead vapors 330-7a from stripper 75-7a are sent to the reboiler of stripper 75-7b. Similarly, the overhead vapors 330-7b from stripper 75-7b are sent to the reboiler of stripper 75-7c. The overhead vapors 330-7c are sent directly to the separator 55-7 as is the overhead condensate 340-7. The amine-stripped water 79-7 is cooled countercurrently and is returned to the fermentor.

Because the vapor density of amine/water is very low at an extraction temperature of 40° C., the compressor 300-7 must be very large leading to very high capital costs. This problem could be overcome by the following approaches:

1) A secondary refrigerant (e.g. ammonia, Freon) could be compressed rather than the amine/water vapors. This approach requires heat exchangers both in the separator 55-7 and mixing vessel 52-7 which adds cost and irreversibilities that negatively impact energy efficiency.

2) Precipitate-free fermentation broth 30-7 could be heated to a higher temperature so the extraction occurs at a higher temperature and the amine/water in mixing vessel 52-7 has a higher vapor density. This approach requires an extra countercurrent heat exchanger to prewarm fermentation broth going to the extractor and precool liquid returning to the fermentor. Also, because there is an approach temperature needed in the countercurrent heat exchanger, extra heat will be needed to fully increase the temperature of the fermentation broth going to the extractor, and extra cooling will be needed to cool the water returning to the fermentors.

3) The fermentation could be operated at thermophilic conditions (e.g. 55° C.) so the extractors operate at a higher temperature resulting in a higher vapor density in mixer 52-7.

4) A highly volatile component (e.g. butane, fluorocarbon) could be added to the water-lean amine 34-7. This volatile component would raise the vapor density in mixer 52-7 allowing a more compact compressor to be employed. The highly volatile component would evaporate in mixer 52-7 and would condense in separator 55-7, so it would mostly circulate. Although some of this volatile component will be in stream 350-7 and will enter the extractors, any volatile component in the amine phase will be recycled, and any volatile component in the water phase will be removed by the strippers; therefore, very little of this volatile component will be lost.

Figure 8:
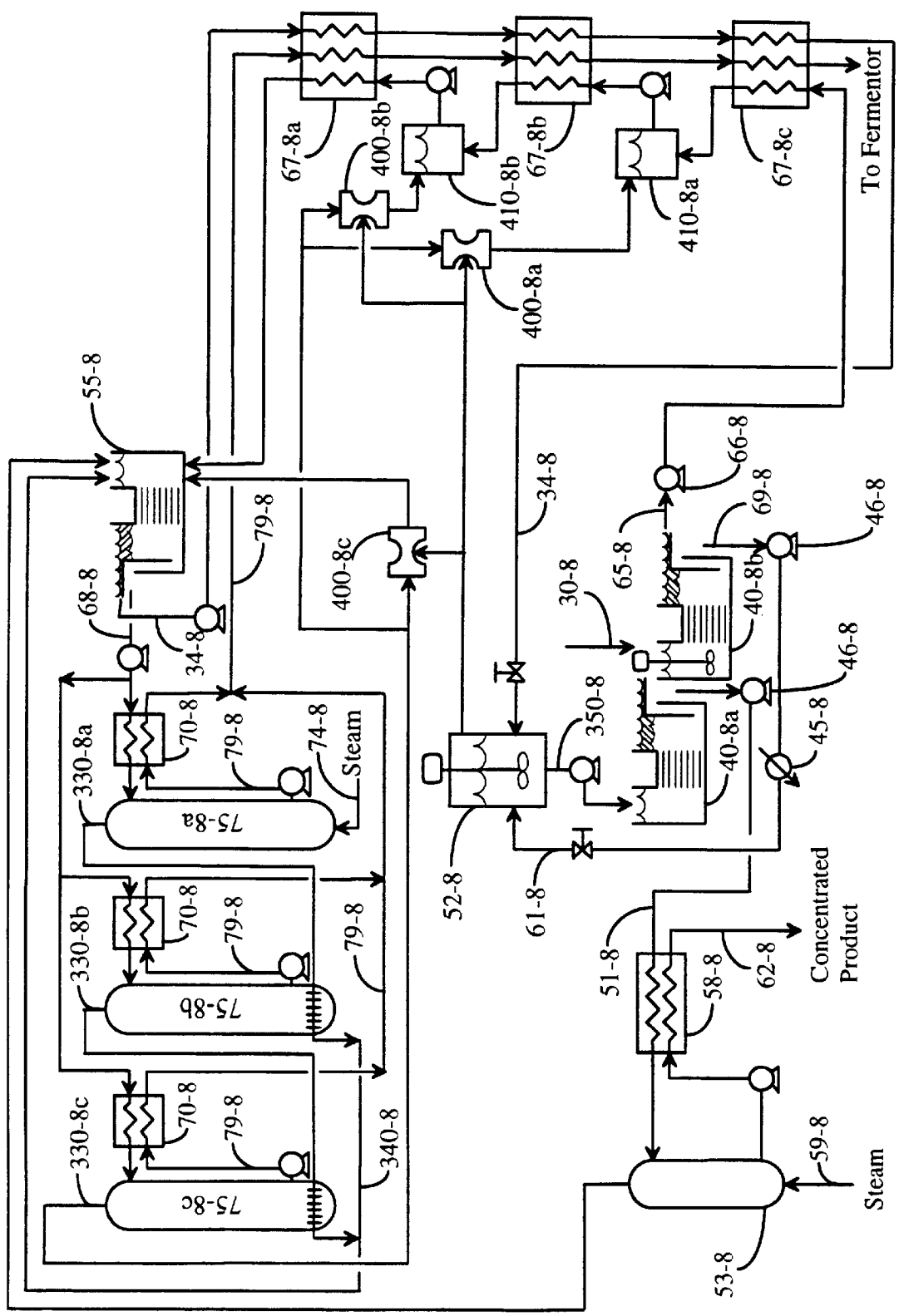
FIG. 8 shows a simplified schematic of Process C which indicates the equipment that affects process energetics.

FIG. 8 shows Process C which uses multiple-stage steam ejectors as heat pumps. High-pressure steam 74-8 (e.g. 180 psig) is put into stripper 75-8a which is the first in a series of multiple-stage strippers. The vapors 330-8c exiting stripper 75-8c are at a high enough pressure (e.g. 100 psig) to provide motive force to the steam ejectors 400-8 which pull a vacuum on mixer 52-8. The vacuum evaporates amine and water from mixer 52-8 which are then compressed and condensed in contactors 410-8 causing water-rich amine 65-8 to increase in temperature. As the temperature rises, water begins to phase out of the water-rich amine, a process that is completed in separator 55-8. Because steam ejectors are inefficient at high compression ratios, the steam ejectors are staged. Steam ejector 400-8a has the lowest compression ratio because the pressure in contactor 410-8a is low. Steam ejector 400-8c has the highest compression ratio because the pressure in separator 55-8 is relatively high. Although FIG. 8 shows three heat pump stages, fewer or more may be used.

Figure 9:
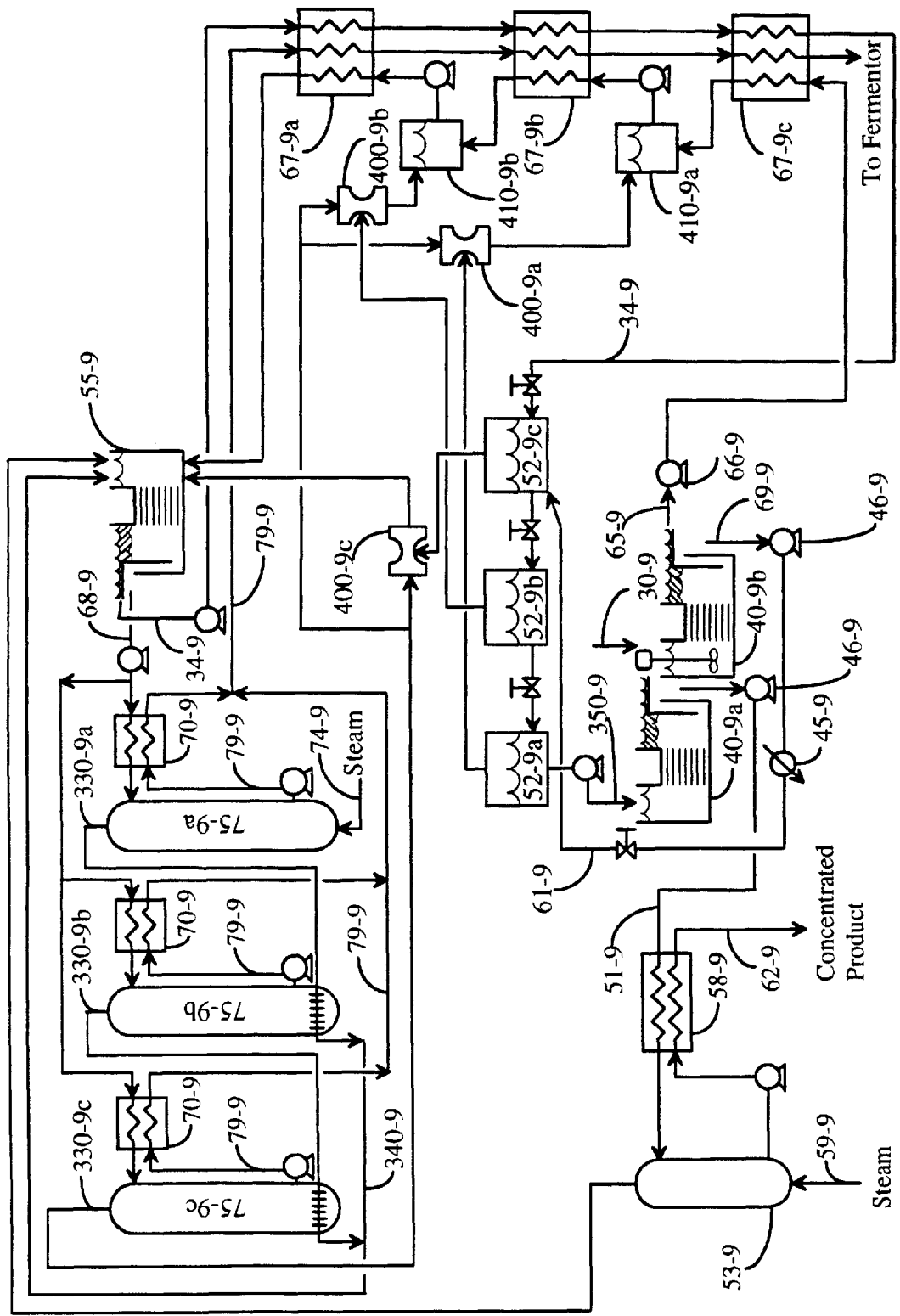
FIG. 9 shows a simplified schematic of a modifiedc version of Process C.

FIG. 9 shows a variation on Process C in which the ejectors 400-9 pull a vacuum on mixers 52-9 in multiple stages. Aqueous solution 61-9 is added to water-lean amine 34-9 in mixer 52-9c. Due to the heat of mixing, the temperature rises in mixer 52-9c, raising its vapor pressure. Using ejector 400-9c, vapors are removed from mixer 52-9c and compressed into separator 55-9. The liquid exiting mixer 52-9c is reduced in pressure and added to mixer 52-9b where vapors are removed using ejector 400-9b and added to contactor 410-9b. A similar process occurs in mixer 52-9a. The advantage of this multi-stage flashing process is that the compression ratio of each ejector 400-9 is reduced, resulting in steam savings.

Figure 10:
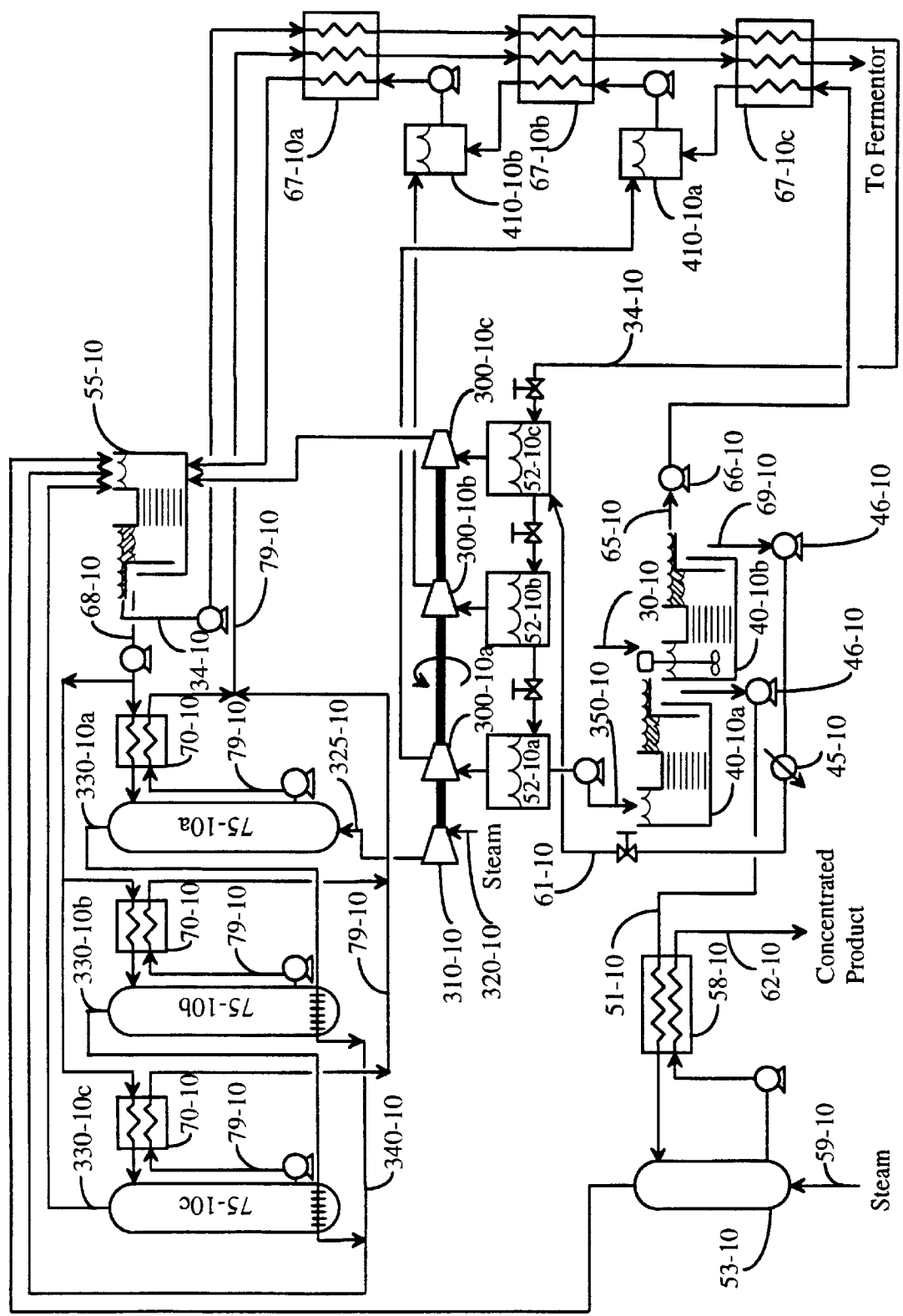
FIG. 10 shows a simplified schematic of a modified version of Process B.

The energy benefits of a multiple-stage heat pump can also be realized by using multiple-stage mechanical compressors instead of the steam ejectors (see FIG. 10). To raise the vapor density, a volatile component (e.g. butane, fluorocarbon, etc.) can be added directly to the water-lean amine. The volatile component would circulate between multiple-stage mixers 52-10 and the separator 55-10 such that very little of the volatile component would be present in the extractors 40-10. In the case of a hydrocarbon volatile component (e.g. butane), it will distribute primarily in the amine phase, helping to push water out in the separator 55-10. In the case of some fluorocarbons, they are substantially immiscible in both water and amine. They have a density higher than water, so they would be drawn off the bottom of the gathering section of separator 55-10 and added directly to mixer 52-10c.

An important consequence of Process C is that it allows recovery of dilute acids without paying a large capital or energy penalty. The liquid residence time in the fermentor is largely determined by the product concentration; lower product concentrations have a short residence time because product inhibition is less. The fermentor volume decreases with shorter liquid residence time; thus, for lower product concentrations, the fermentor can be smaller.

The energy estimates shown in Table 1 were calculated using a simplifying assumption that the amount of water that phases out of the amine increases linearly with temperature. In actuality, for a single degree increase in temperature, more water phases out at low temperatures than at high temperatures. As a consequence, more of the heat pump energy will be needed at low temperatures where the compression ratio is smaller and less steam is needed; therefore, the simplifying linear assumption will give a worst-case analysis. The real situation will require less energy than these projections.

The unique separation technique described in this invention provides a commercially viable method for separating and concentrating carboxylate salts formed during fermentation with recycle of all streams and minimal waste.

Concentrated solutions of carboxylate salts obtained by the method of this invention may be further concentrated by evaporation, dried or converted to concentrated carboxylic acid solutions as will be readily apparent to those skilled in the art. Suitable processes for further converting of the concentrated carboxylic acid salt solution of this invention into the desired product are described in U.S. Ser. No. 08/885,896; now U.S. Pat. No. 6,043,392 entitled "Method for Conversion of Biomass to Chemicals and Fuels", filed concurrently herewith and incorporated herein by reference in its entirety.

We claim:

1. An extraction tank comprising
    a mixing section adapted for mixing a first fluid input stream and a second fluid input stream;
    a separating section comprising a plurality of plates parallel to each other and in substantially horizontal orientation; and
    a gathering section adapted for collecting an upper fluid layer and a lower aqueous fluid layer, having two weirs, a first weir being in fluid communication with the upper fluid layer and a second weir in fluid communication with the lower layer, the two weirs being in fluid communication with a first collection structure and a second collection structure, respectively;
    wherein one end of the parallel plates of the separating section is in fluid communication with the mixing section and an other end of the parallel plates is in fluid communication with the gathering section.

2. The extraction tank of claim 1, wherein the parallel plates are rippled sheets.

3. The extraction tank of claim 1, wherein the end of the plurality of plates in fluid communication with the gathering section slopes such that a lower plate extends further into the gathering section than the immediately higher plate.

4. The extraction tank of claim 1, wherein the gathering section further includes a well to collect settled solids and facilitate their removal.

5. The extraction tank of claim 1, where a pump removes material from the interface of the two fluids in the gathering section, whereby accumulated solids are removed.

6. The extraction tank of claim 1, wherein the n mixing section contains a plurality of rotating shafts having projections, projections of respective shafts being interspersed such that even, gentle mixing is obtained.

7. The extraction tank of claim 1, further comprising means for introducing a large flowrate of aqueous layer to the plurality of parallel plates whereby settled solids are flushed therefrom, and means for collecting the aqueous layer, wherein the solids settle for removal.

8. The extraction tank of claim 1, in which sections of the plurality of parallel plates can cleaned of settled solids by isolating said sections and introducing a large flowrate of aqueous layer, collecting the aqueous flow in the gathering section, and recovering settled solids from the gathering section.

9. A method of extracting a solute component from a first fluid containing said solute component into a second fluid, wherein said first fluid and said second fluid are immiscible and have different densities, said method comprising
    i) feeding said first and second fluids into an extraction tank, wherein the extraction tank comprises:
        a mixing section adapted for mixing a first fluid input stream and a second fluid input stream;
        a separating section comprising a plurality of plates parallel to each other and in substantially horizontal orientation; and
        a gathering section adapted for collecting an upper fluid layer and a lower aqueous fluid layer, having two weirs, a first weir being in fluid communication with the upper fluid layer and a second weir in fluid communication with the lower layer, the two weirs being in fluid communication with a first collection structure and a second collection structure, respectively;
        wherein one end of the parallel plates of the separating section is in fluid communication with the mixing section and an other end of the parallel plates is in fluid communication with the gathering section, and
    ii) collecting the respective fluid from the first and second collection structures.

* * * * *

UNITED STATES PATENT AND TRADEMARK OFFICE
CERTIFICATE OF CORRECTION

PATENT NO.     : 6,478,965 B1
DATED          : November 12, 2002
INVENTOR(S)    : Mark T. Holtzapple et al.

It is certified that error appears in the above-identified patent and that said Letters Patent is hereby corrected as shown below:

Title page,
Item [57], ABSTRACT,
Line 5, after "30°" delete "C." and insert -- C -- and after "55°" delete "C." and insert -- C --.

Column 3,
Line 14, after "3,424,675.)" delete "psCarboxylic Acids from Biomass" and insert heading titled -- Carboxylic Acids from Biomass --.
Lines 25 and 32, the word "in situ" should be italicized.

Column 4,
Line 2, after "carboxylate" the word "salt" should be underlined.
Line 59, after "schematic of a" delete "modifiedc" and insert -- modified --.

Column 5,
Line 7, after "(TEA) and" the letters "N, N" should be italicized.
Line 11, after "20-30°" delete "C." and insert -- C --.
Line 24, delete "10" before the number "1".

Column 6,
Line 19, after "10°" delete "C." and insert -- C --.
Line 25, at the beginning of the sentence, delete "C." and insert -- C --.
Line 26, after "(55°" delete "C." and insert -- C --.
Line 29, the word "Clostridium thermocellum" should be italicized.
Line 37, after "40°" delete "C." and insert -- C -- and after "55°" delete "C." and insert -- C --.
Line 54, after "55°" delete "C." and insert -- C --.

Column 10,
Line 31, after "h·°" delete "F." and insert -- F --.
Line 35, after "6.5°" delete "C." and insert -- C -- and after "4.1°" delete "C." and insert -- C --.
Line 43, after "1°" delete "C." and insert -- C --.
Line 44, after "10.9°" delete "C." and insert -- C --.
Line 66, after "40°" delete "C." and insert -- C --.
Line 67, after "60°" delete "C." and insert -- C --.

UNITED STATES PATENT AND TRADEMARK OFFICE
CERTIFICATE OF CORRECTION

PATENT NO. : 6,478,965 B1
DATED : November 12, 2002
INVENTOR(S) : Mark T. Holtzapple et al.

It is certified that error appears in the above-identified patent and that said Letters Patent is hereby corrected as shown below:

Column 11,
Line 20, after "40°" delete "C." and insert -- C -- and after "60°" delete "C." and insert -- C --.
Lines 30 and 45, after "40°" delete "C." and insert -- C --.

Column 12,
Line 6, after "40°" delete "C." and insert -- C --.
Line 28, after "55°" delete "C." and insert -- C --.

Signed and Sealed this

Twenty-third Day of December, 2003

JAMES E. ROGAN
*Director of the United States Patent and Trademark Office*